Sept. 9, 1958 A. O. WILD Plant Pat. 1,747

ELM TREE

Filed Aug. 19, 1957 3 Sheets-Sheet 1

INVENTOR.
Arthur O Wild
BY
Robert Cobb
ATTORNEYS

INVENTOR.
Arthur O. Wild
BY
Robb & Robb
ATTORNEYS

INVENTOR.
Arthur O. Wild
BY
Robert Robb
ATTORNEYS

United States Patent Office

Plant Pat. 1,747
Patented Sept. 9, 1958

1,747

ELM TREE

Arthur O. Wild, Sarcoxie, Mo., assignor to Sarcoxie Nurseries (Wild Bros. Nursery Company), Sarcoxie, Mo., a partnership Application August 19, 1957, Serial No. 679,113

1 Claim. (Cl. 47—59)

The present invention relates to a new and distinct variety of elm tree which was originated by me as a cultivated and selected seedling of the variety known as "Coolshade" (unpatented) which was a hybrid elm of uncertain parentage, but believed to have derived from a cross of *"Ulmus pumila"* (unpatented) X *"Ulmus fulva"* (unpatented), the latter variety being sometimes called *"Ulmus rubra,"* but more commonly known as "Slippery Elm" or "Red Elm."

Most hybrid elms tend to be crooked or have their branches poorly arranged, and thus make a flat or very ill-shaped tree, and the crotches of the tree tend to split when subjected to the weight of ice or snow. These undesirable characteristics prevailed in the parent variety "Coolshade," as well as in most Chinese elms, and despite the desirable leafy characteristic of the parent variety, it was not entirely satisfactory for street and lawn plantings. Accordingly, I endeavoured to develop an improved elm which was not subject to the adverse characteristics referred to above, and my objective was fully achieved through the growing of a considerable number of seedlings of the variety "Coolshade" from which the new variety was selected as being a vastly superior variety, as evidenced by the following outstanding characteristics which are found in my new variety:

(1) Easier growth and cultivation than the parent variety and other hybrid elms;

(2) An abundant and deep root system which is much stronger than that of *"Ulmus pumila"*;

(3) A straight and symmetrical trunk or bole which maintains its diameter remarkably well;

(4) Branches arranged on the trunk or bole in such a manner as to eliminate or substantially minimize weak crotches, thereby preventing damage by ice and snow under conditions which have heretofore virtually stripped other hybrid elms of their limbs and branches;

(5) Abundant and well-distributed leaves, averaging about 3 inches in length;

(6) Rapid growth; and (7) Exceptional winter-hardiness and toughness.

Asexual reproduction of my new variety by both budding and grafting as performed by me at Sarcoxie, Missouri, shows that the foregoing characteristics and distinctions come true to form and are established and transmitted through succeeding propagations.

Figure 1:
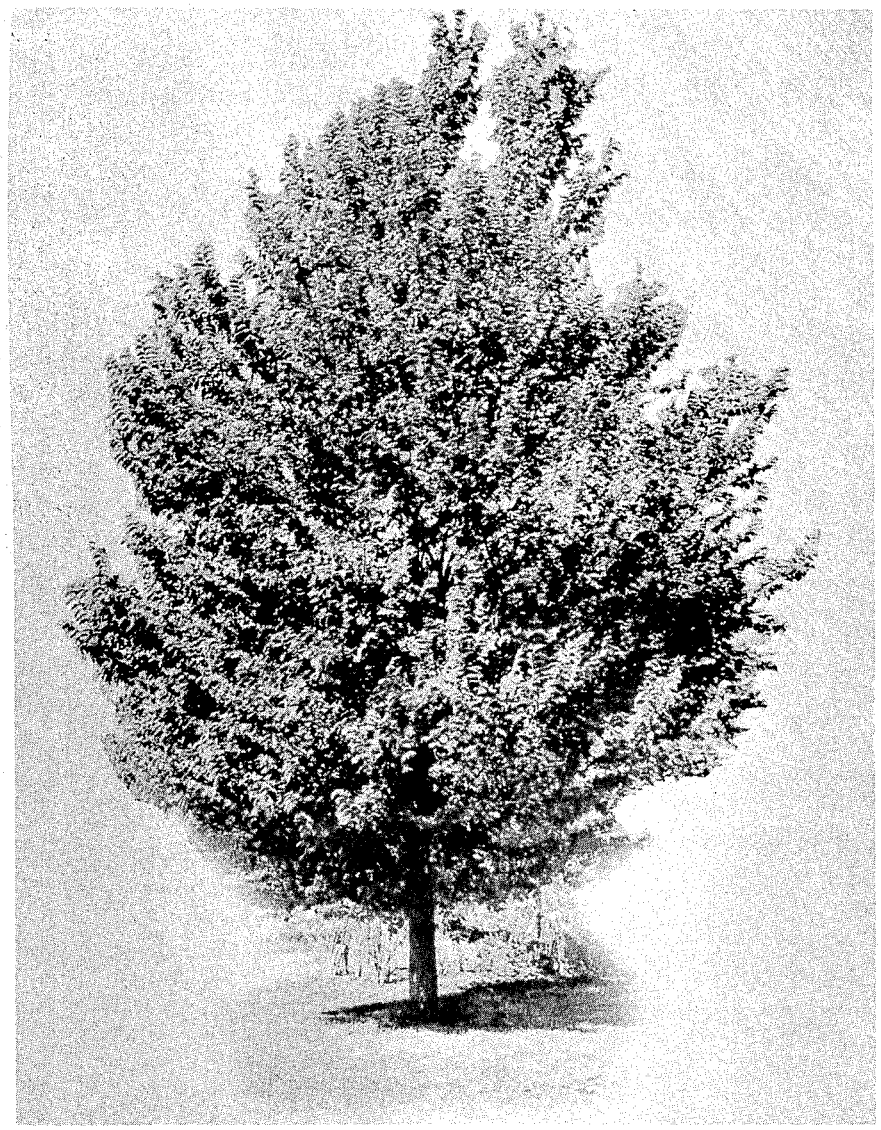
Fig. 1 shows a typical mature tree of my new elm variety and depicting the general form and leafiness thereof.
Figure 2:
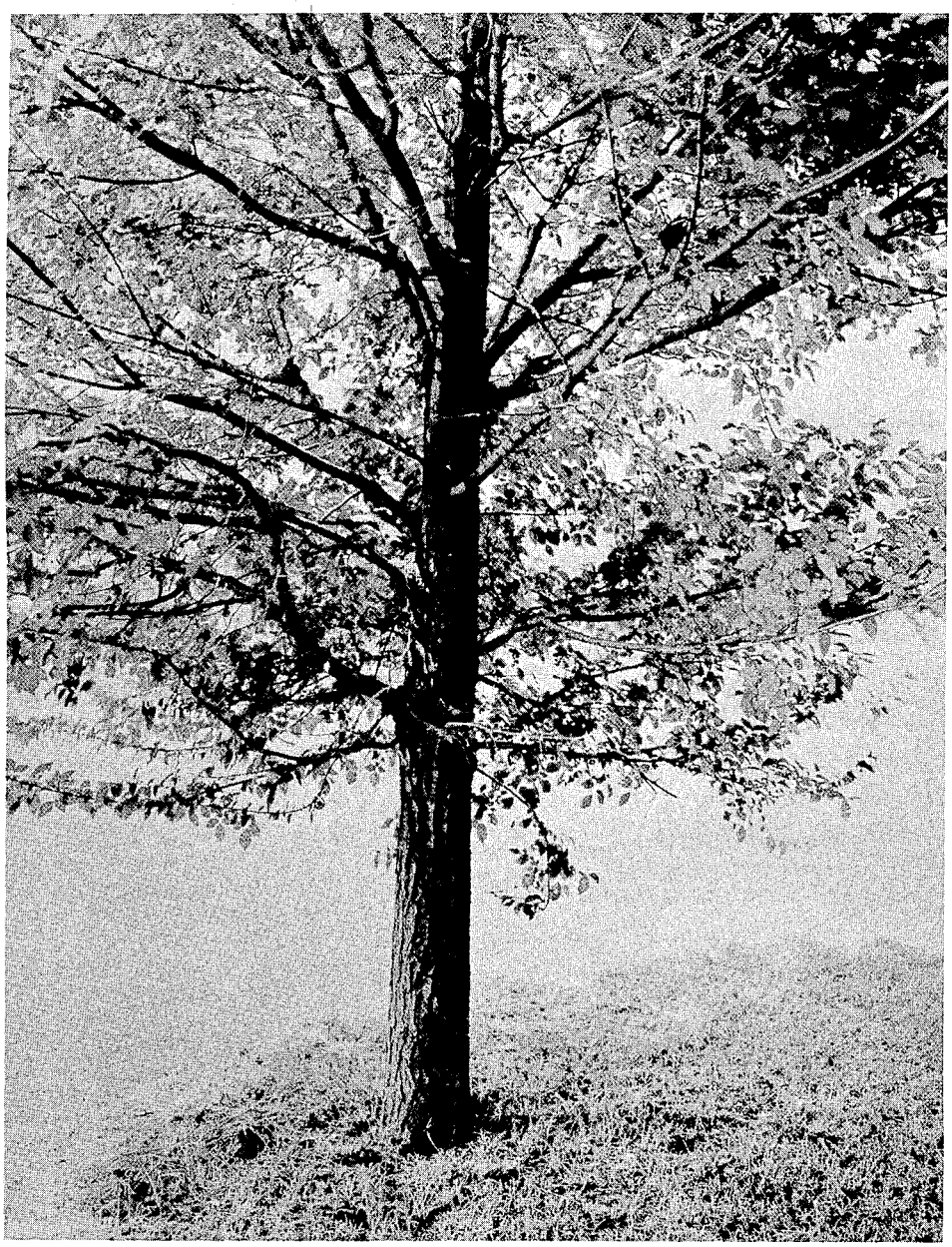
Fig. 2 illustrates more particularly the straight trunk and the strong branching habits of the tree.
Figure 3:
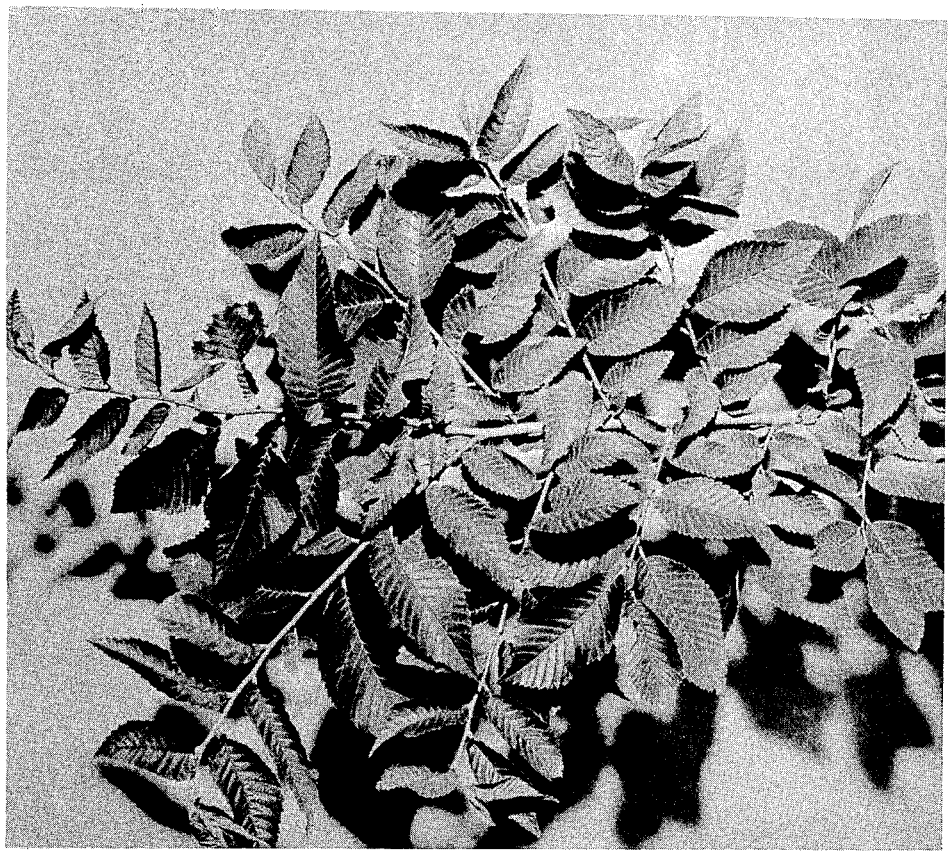
Fig. 3 shows on a somewhat enlarged scale typical foliage specimens and their relatively dense arrangement on a short branch section as selected for illustrative purposes.

The following is a detailed description of my new variety:

Parentage: Seedling of "Coolshade."

Propagation: Holds its distinguishing characteristics through succeeding propagations by both budding and grafting.

Locality where grown and observed: Sarcoxie, Missouri.

Tree: Tall; symmetrical; vigorous; upright; dense; rapid growth; hardy.

Trunk: Sturdy; straight; symmetrical; smooth.

Branches: Thick; symmetrical; tough; form strong crotches with trunk.

Leaves: Finely serrated.

*Length.*—About 3 inches.

*Width.*—About 1¾ inches.

*Color.*—Medium Green (somewhat darker than the leaves of Chinese elms).

Disease resistance: Moderately resistant to Dutch Elm disease as determined by innoculation tests and reports by the U. S. Department of Agriculture.

Use: Street and lawn plantings.

I claim:

A new and distinct variety of elm tree, substantially as herein shown and described, characterized particularly as to novelty by the ease of its growth and cultivation, its rapid growth, its abundant and deep root system, its straight and symmetrical trunk, its tough and thick branches and their formation of strong crotches with the trunk, its abundant foliage, and its winter hardiness.

No references cited.